(12) United States Patent
Kim et al.

(10) Patent No.: US 9,046,510 B2
(45) Date of Patent: Jun. 2, 2015

(54) MEMBRANE AND METHOD OF FABRICATING THE SAME

(75) Inventors: Jin Kon Kim, Gyeongju (KR);
Sangshin Jang, Gwangyang (KR);
Seung Yun Yang, Daegu (KR); Gumhye Jeon, Jinhae (KR); Won Jong Kim, Pohang (KR); Sejin Son, Pohang (KR);
Hyunwoo Kim, Jecheon (KR)

(73) Assignee: POSTECH ACADEMY-INDUSTRY FOUNDATION, Pohang (KR)

( * ) Notice: Subject to any disclaimer, the term of this patent is extended or adjusted under 35 U.S.C. 154(b) by 455 days.

(21) Appl. No.: 13/396,078

(22) Filed: Feb. 14, 2012

(65) Prior Publication Data
US 2013/0040127 A1    Feb. 14, 2013

(30) Foreign Application Priority Data

Aug. 12, 2011    (KR) .................. 10-2011-0080828

(51) Int. Cl.
*B31D 3/00*    (2006.01)
*G01N 33/487*    (2006.01)
*B82Y 40/00*    (2011.01)
*B82Y 30/00*    (2011.01)

(52) U.S. Cl.
CPC ........... *G01N 33/48721* (2013.01); *B82Y 40/00* (2013.01); *B82Y 30/00* (2013.01)

(58) Field of Classification Search
CPC ... B82Y 30/00; B82Y 40/00; G01N 33/48721
USPC ....................................... 216/56, 83; 977/888
See application file for complete search history.

(56) References Cited

U.S. PATENT DOCUMENTS

| | | | | |
|---|---|---|---|---|
| 7,438,193 B2 * | 10/2008 | Yang et al. | ..................... | 210/490 |
| 8,137,569 B2 * | 3/2012 | Harnack et al. | .................... | 216/2 |
| 2004/0124092 A1 * | 7/2004 | Black et al. | .................... | 205/363 |
| 2004/0149688 A1 * | 8/2004 | Fuchs et al. | ..................... | 216/56 |
| 2009/0130380 A1 * | 5/2009 | Asakawa et al. | ............. | 428/116 |
| 2011/0042301 A1 * | 2/2011 | Zhang et al. | ............. | 210/500.21 |

OTHER PUBLICATIONS

Seung Y. Yang, et al., "Nanoporous Membranes with Ultrahigh Selectivity and Flux for the Filtration of Viruses", Advanced Materials, vol. 18, p. 709-712, (Feb. 16, 2006).
Ivan Vlassiouk, et al., "Direct Detection and Separation of DNA Using Nanoporous Alumina Filters", Langmuir, vol. 20, No. 23, p. 9913-9915 (Nov. 2004).
Seung Yun Yang, et al., "DNA-Functionalized Nanochannels for SNP Detection", Nano Letters, pp. 1032-1035, Feb. 16, 2011.

* cited by examiner

*Primary Examiner* — Shamim Ahmed
(74) *Attorney, Agent, or Firm* — Lexyoume IP Meister, PLLC

(57) ABSTRACT

A membrane according to the present invention includes a support member and a polymer layer disposed on the support member and including a plurality of nano pores each having an inner wall formed of a block-structured polymer material of which the end thereof is substituted by a functional group.

5 Claims, 8 Drawing Sheets

MEMBRANE AND METHOD OF FABRICATING THE SAME

CROSS-REFERENCE TO RELATED APPLICATION

This application claims priority to and the benefit of Korean Patent Application No. 10-2011-0080828 filed in the Korean Intellectual Property Office on Aug. 12, 2011, the entire contents of which are incorporated herein by reference.

BACKGROUND OF THE INVENTION (a) Field of the Invention

The present invention relates to a membrane, and particularly, it relates to a membrane including a nano pore.

(b) Description of the Related Art

In DNA analysis, distinguishment and quantification of a single nucleotide polymorphism has been required for detection of the single nucleotide polymorphism, As the most abundant genetic marker in DNA, the single nucleotide polymorphism has been widely used for forming a gene map, diagnosis of genetic disease, and development of medicine substitution materials.

Various methods are used to detect the single nucleotide polymorphism, and the methods include a biochemical method using enzymes, a selective ligation method using a fluorescent marker gene and an enzyme, an electrophoretic method using an additive, a method using a nano pore having molecular probe, and the like.

A disclosed method for analyzing DNA using nano pores includes a method for forming nano pores using electrons or ion-beams, a track-etching method, and the like.

The method has merits of simplicity and promptness compared to other methods because selective coupling force such as DNA hybridization is used using the molecular probe in a wall wide of the nano pore.

However, the method requires two processes for reforming of a nano pore surface to fix a necessary molecular recognition agent (MRA) for forming and analyzing of nano pores, and has drawbacks of reproducibility and density of the nano pores, difficulty in introduction of a specific functional group to a wall side of the nano pore, and long reaction time.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method for forming nano pores for convenient DNA analysis providing a specific functional group in a wall side of the nano pores.

A membrane according to an exemplary embodiment of the present invention includes a support member and a polymer layer disposed on the support member and including a plurality of nano pores each having an inner wall formed of a block-structured polymer material of which the end thereof is substituted by a functional group.

The functional group may be at least one of —COOH, —NH$_2$, and —SH.

The block-structured polymer material may be a PMMA block.

The thickness of the polymer layer may be 50 nm to 100 nm.

The nano pores of the polymer layer may be distributed with density of $10^{11}$ nano pores/cm2.

A membrane manufacturing method according to the exemplary embodiment of the present invention includes: forming an alignment layer with PS-ran-PMMA on a substrate including a sacrificial layer; forming a polymner layer by coating a solution including PS-b-PMMA-diCOOH on the alignment layer; and forming a plurality of nano pores, each having an inner wall formed of a PMMA block in the polymer layer by soaking the polymer layer in an acetic acid.

The solution including PS-b-PMMA-diCOOH further includes a PMMA single polymer, and the solution including PS-b-PMMA-diCOOH is formed by mixing a polystyrene-block-poly(methyl methacrylate) block with a p-toluene-sulfonic acid and hydrolyzing the mixture at 100° C. for 12 hours.

The forming of the polymer layer further includes coating the solution and performing heat treatment, and the heat treatment may be performed at 170° C. for 24 hours After the forming of the nano pores, eliminating the sacrificial layer by etching may be further included, and the sacrificial layer may be formed of silicon oxide and eliminated by etching with a hydrofluoric acid solution.

After the sacrificial layer is eliminated, fixing the polymer layer on a support member may be further included.

With the method according to the present invention, a nano pore including a functional group can be easily formed.

In addition, a material can be detected and separated according to affinity between DNAs in the nano pore using the nano pore according to the present invention so that a membrane that separates DNAs can be formed without using an enzyme or a chemical/electric signal device.

Further, the thickness of the membrane is slim and density of the nano pores is high so that single nucleotide polymorphism analysis can be performed with high efficiency.

DETAILED DESCRIPTION OF THE EMBODIMENTS

Figure 1:
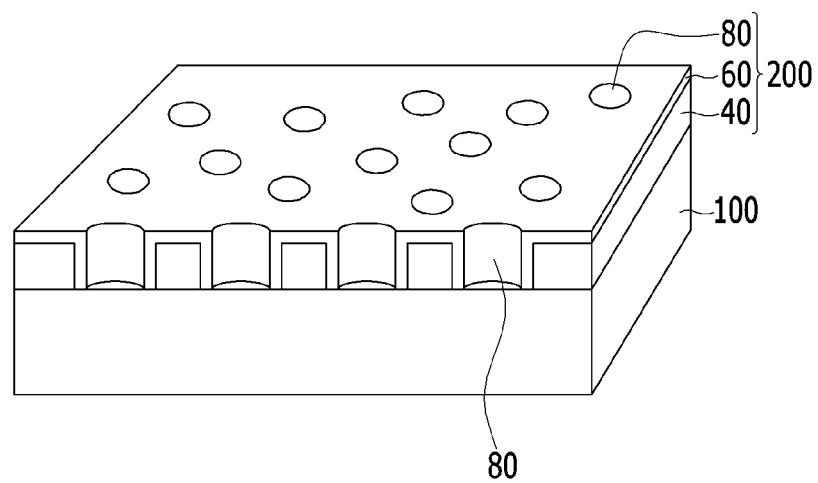
FIG. 1 is a schematic perspective view of a membrane including a nano pore according to an exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Hereinafter, a membrane including nano pores according to an exemplary embodiment of the present invention will be described with reference to the accompanying drawings.

FIG. 1 is a schematic cross-sectional view of a membrane including nano pores according to an exemplary embodiment of the present invention.

As shown in FIG. 1, the membrane according to the present exemplary embodiment includes a support member 100 and a polymer layer 200 formed on the support member 100 and including nano pores 80.

The support member 100 may be a polysulfone membrane and supports the polymer layer 200.

The polymer layer 200 includes pipe-type pores, each having a nano-sized diameter. The diameter of each nano pore 80 is about equal to or less than 15 nm and dispersion density of the nano pores is greater than or equal to $10^{11}$ nano pores/cm2.

In addition, an inner wall of the polymer layer 200 includes a polymer material layer having a block structure in which an end terminal thereof is substituted by a functional group and other polymer material layer that does not include a functional group.

For convenience of description, the polymer material layer having the block structure substituted by the functional group is called a first polymer material layer and the other polymer material layer not having the functional group is called as a second polymer material layer.

In further detail, the polymer layer 200 includes a second polymer material layer 40 and a first polymer material layer 60 forming an inner wall of the nano pore 80 by being disposed in a side wall of the second polymer material layer 40 and disposed on an upper side of the second polymer material layer 40. The first polymer material layer 60 may be formed of a block such as polymethyle methacrylate (PMMA) and the end terminal is substituted by one of functional groups, for example, one of functional groups having —COOH, —NH$_2$, or —SH charges.

The second polymer material layer 40 may be formed of a PS block 40.

As described, various analyses can be performed using the nano pore 80 having the inner wall substituted by the functional group. For example, a single nucleotide polymorphism DNA can be easily analyzed using the nano pore 80 having an inner wall substituted by a carboxyl group.

Figure 2:
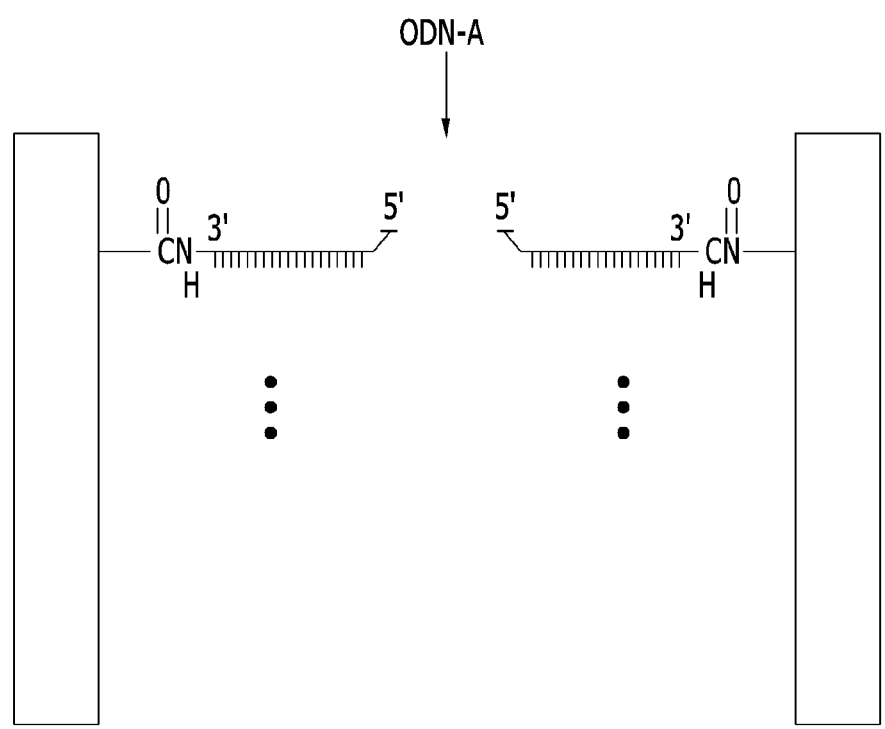
FIG. 2 to FIG. 4 are schematic cross-sectional views for description of a method for analyzing a single nucleotide polymorphism using the membrane according to the exemplary embodiment of the present invention.
Figure 3:
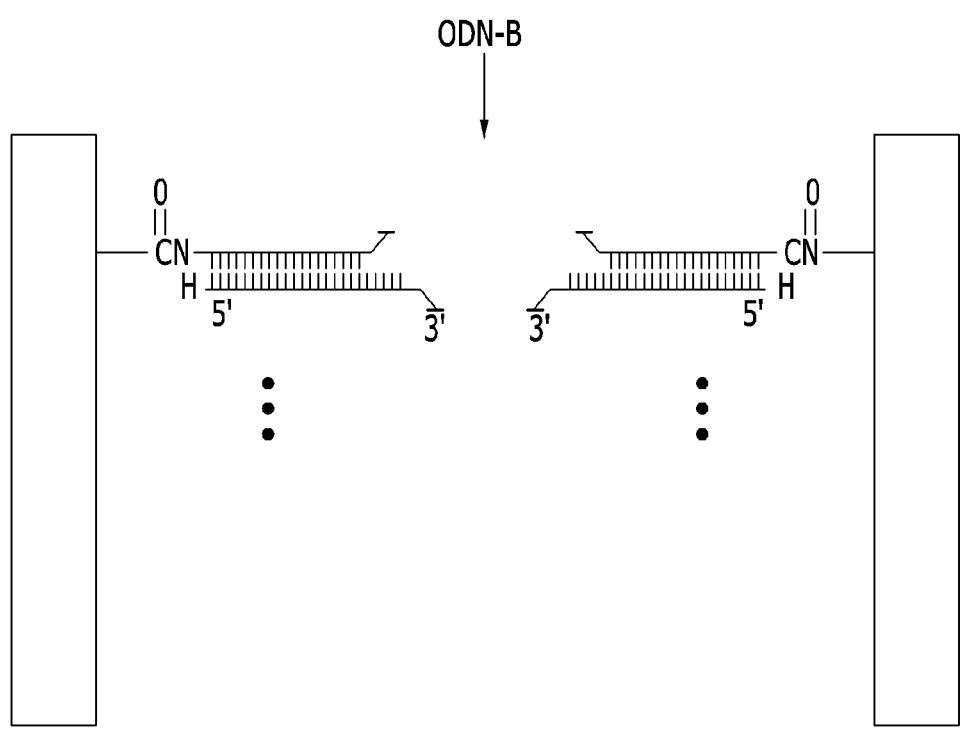
Figure 4:
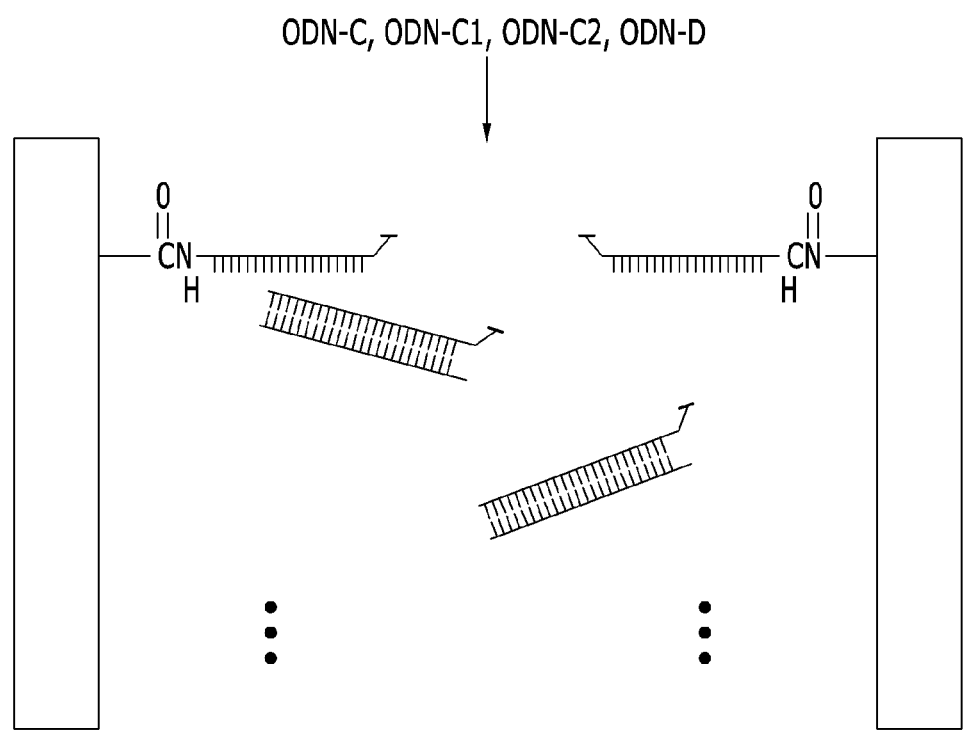
Figure 5:
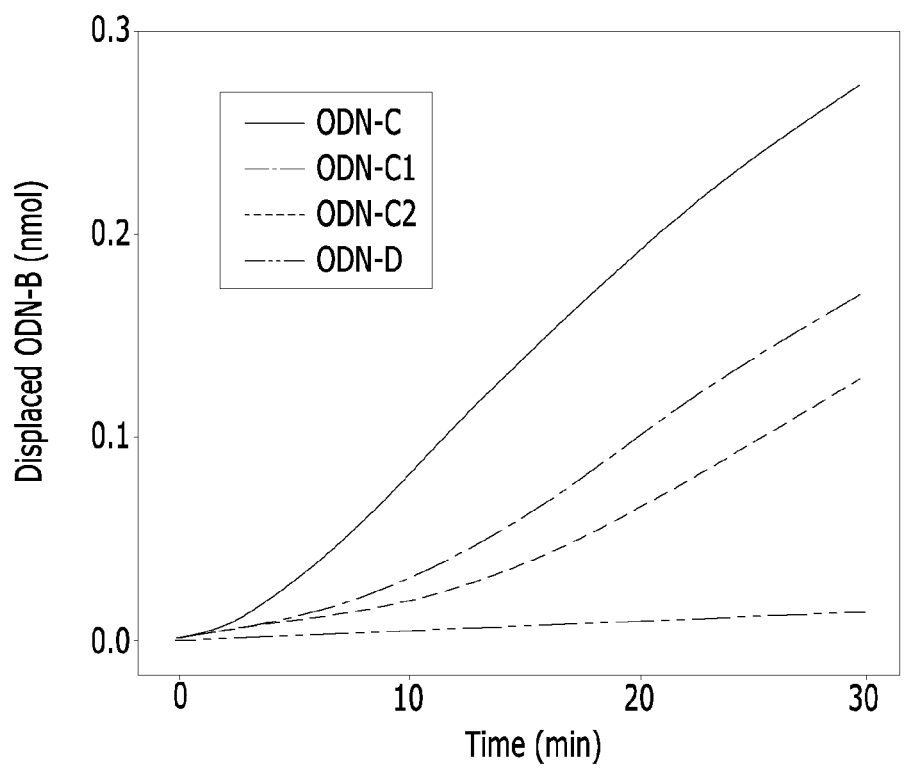
FIG. 5 is a graph of efficiency measurement of various single nucleotide polymorphisms according to the exemplary embodiment of the present invention.

FIG. 2, FIG. 3, and FIG. 4 are schematic cross-sectional views for description of a method for analyzing a single nucleotide polymorphism using the membrane according to the exemplary embodiment of the present invention, and FIG. 5 is a graph of measurement of efficiency of various single nucleotide polymorphisms according to the exemplary embodiment of the present invention.

As shown in FIG. 2, an oligodeoxynucleotide solution having amine substituted 3'end (hereinafter, referred to as ODN-A) is dropped to the membrane having the nano pore 80 formed of an inner wall substituted by the carboxyl group.

In this case, ODN-A is a 14 base oligodeoxynucleotide having carboxy-fluorescein (FAM) is labeled to the 5'end. Here, FAM is a luminous material. A nucleotide sequencing of the ODN-A is 5'-FAM-GAA ATA ATC AAT GA-NH$_2$-3'.

Then, a covalent bond is formed in the inner wall of the nano pore 80 from reaction between the carboxyl group and the ODN-A.

Next, as shown in FIG. 3, 19 base oligodeoxynucleotide (hereinafter, referred to as ODN-B) formed of 5 nucleotides of 3'end, having nucleotide that is complementary with the 14 base of ODN-A and maintained without being additionally hybridized is dropped in the membrane of which ODN-A is included in its inner wall.

In this case, the ODN-B is 5'-TCA TTG ATT ATT TCC CAG G-TAMRA-3'.

Since a luminous material is labeled to ODN-B, a hybridization efficiency of ODN-A and ODN-B can be measured by measuring the amount of ODN-A and the amount of ODN-B in the inner wall of the membrane through a measured fluorescence degree.

With such a method, a different type of single nucleotide polymorphism can be found, and this will be described in detail.

First, a solution of ODN-C corresponding to all of the 19 bases of ODN-B, a solution of ODN-C1 having one mismatch at an end terminal among the 19 bases, a solution of ODN-C2 having one mismatch around the middle, and a solution of ODN-D including non-complementary nucleotide sequencing are prepared.

Next, as shown in FIG. 4, the ODN-C solution is dropped to the membrane including the nano pore 80 formed of hybridization of ODN-A and ODN-B. In addition, like the method for dropping the ODN-C solution, the ODN-C1 solution, the ODN-C2 solution, and the ODN-D solution are respectively dopped to the membrane including the nano pore 80 formed of hybridization of ODN-A and ODN-B.

In this case, ODN-C is 5'-CC GGG AAA TAA TCA ATG A-3', ODN-C1 is 5'-CCT GGG AAA TAA TCA ACG A-3', ODN-C2 is 5' CCT GGG AAA TAT TCA ATG A-3', and ODN-D is 5'-TTT TTT TTA ACC CCA ACC CC-3'.

After that, the graph of FIG. 5 can be acquired by measuring a fluorescence degree and acquiring the amount of ODN-B substituted therefrom.

In the graph of FIG. 5, ODN-C, ODN-C1, ODN-C2, ODN-D respectively have different displace efficiency.

Referring to the graph of FIG. 5, ODN-C fully matched with the ODN-B has replacement efficiency that is 60% higher than that of ODN-C1 and ODN-C2. Here, ODN-C1 and ODN-C2 have one mismatch with the ODN-B. In addition, ODN-C1 having the mismatch at the end thereof is higher replacement efficiency than ODN-C2 having the mismatch in the middle thereof.

Meanwhile, ODN-D including the nucleotide sequencing that is not complementary with ODN-B has almost zero replacement efficiency.

As described, a single nucleotide polymorphism according to a location of the mismatch can be found by using the membrane including the nano pore 80 formed of the inner wall substituted according to the present exemplary embodiment.

A method for forming the above-described membrane according to the exemplary embodiment of the present invention will now be described in detail with reference to FIG. 6 to FIG. 8.

Figure 6:
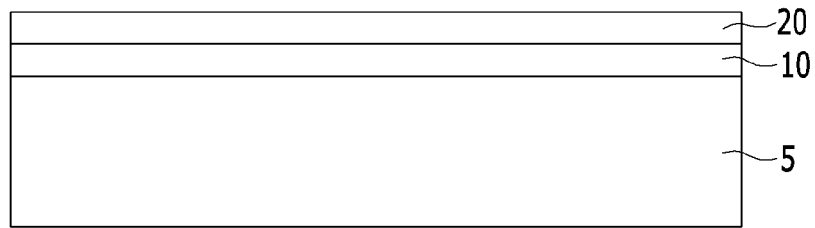
FIG. 6 to FIG. 8 are sequential cross-sectional views of a method for manufacturing the membrane according to the exemplary embodiment of the present invention.
Figure 7:
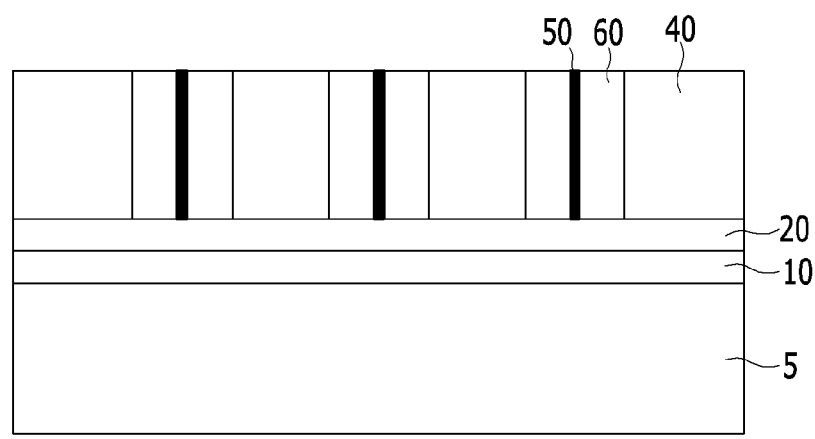
Figure 8:
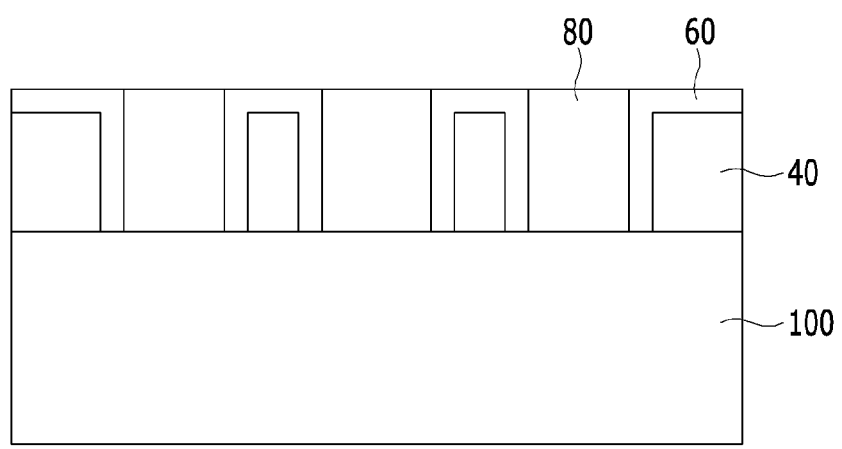

FIG. 6 to FIG. 8 sequentially show a method for manufacturing the membrane according to the exemplary embodiment of the present invention.

First, as shown in FIG. 6, an alignment layer 20 is formed by spin-coating poly (styrene-ran-methyl methacrylate) on a substrate.

The substrate functions to transfer to the support member 100 supporting the polymer layer 200 (to be described later), and may be a silicon (Si) substrate. The alignment layer 20 helps a polymer block (to be described later) be aligned perpendicularly to the substrate 5.

A sacrificial layer 10 is formed between the substrate 5 and the alignment layer 20, and the sacrificial layer 10 is provided for separation of the polymer layer 200 and the substrate 5 and may be formed of a material that can be easily eliminated by an etchant. In the exemplary embodiment of the present invention, an oxide layer is formed with a thickness of 300 nm. Alternatively, a native oxide layer formed on the substrate may be used.

Next, the polymer layer 200 is formed by spin-coating a mixture solution on the alignment layer 20 and then performing heat treatment thereon. The polymer layer 200 includes a phase-separated PS block 40 and a pillar-shaped PMMA block 60.

For the mixture solution, a polystyrene-block-poly(methyl methacrylate) (hereinafter, referred to as PS-b-PMMA-diE) block copolymer having a di-tert-butyl ester terminated and a p-toluenesulfonic acid are hydrolyzed at 100° C. for 12 hours and then the PS-b-PMMA-diE terminated is substituted by di-carboxylic acid such that PS-b-PMMA-diCOOH is manufactured. Then, a homopolymer is mixed into a PS-b-PMMA-diCOOH block copolymer solution to form the mixture solution.

PS-b-PMMA-diCOOH according to the present exemplary embodiment refers a copolymer that can form a phase for each block forming a phase-separated copolymer through a self-assembly process. PS-b-PMMA-diCOOH is formed of the PS block 40 and the PMMA block 60 terminated by the carboxyl group (—COOH).

A ratio of the volume of the PS block 40 of the phase-separated copolymer according to the exemplary embodiment of the present invention is two times greater than that of the PMMA block 60. That is, when the volume ratio of the PMMA block 60 is 3, the volume ratio of the PS block 40 may be 7 to 8.

Since the volume of the block in the same area is changed according to the molecular weight of the PMMA block 60 and the molecular weight of the PS block 40, the size of the pillar-shaped PMMA block 60 can be controlled by controlling the molecular weights of the two blocks 40 and 60. Accordingly, the density of the nano pore can be controlled.

Meanwhile, when the thickness of the polymer layer 200 is decreased, time for holding DNA is shortened so that measurement may become inaccurate, and when the thickness of the polymer layer 200 is increased, the length of the nano pore 80 is extended so that pressure and time for the solution to pass through the nano pore 80. Accordingly, the polymer layer 200 may have a thickness of about 50 nm to 100 nm.

In this case, the heat treatment may be performed at 170° C. for 24 hours.

The single polymer 50 may be poly(methyl methacrylate), and helps the PMMA block 60 self-assembled in a direction perpendicular to the substrate 50 and thus may be omitted.

Meanwhile, the block copolymer having the carboxyl group is manufactured in the mixture solution according to the exemplary embodiment of the present invention, but a —NH$_2$ or —SH terminated block copolymer may be manufactured from condensation reaction between -diCOOH and a material of a diamine group, as necessary.

Then, as shown in FIG. 7, the substrate 5 having pores is eliminated by soaking the substrate 5 in an etching solution.

A hydrofluoric acid (HF) may be used as the etching solution, and the substrate 5 and the polymer layer 200 can be easily separated by etching the sacrificial layer formed on the substrate. The hydrofluoric acid is diluted with concentration of 10 vol % to 20 vol %. Together with the etching of the sacrificial layer, the alignment layer 20 is separated from the polymer layer 200 and then eliminated with the etching solution.

Then, the support member 100 is attached to a lower portion of the separated polymer layer 200. The support member 100 is picked up to locate the polymer layer 200 on the support member 200 when the substrate 5 and the polymer layer 200 are separated by the hydrofluoric acid solution such that the support member 100 is fixed on the support member 100.

Then, as shown in FIG. 8, the substrate 5 in which the polymer layer 200 is formed is soaked in an acetic acid to form a membrane including the nano pores 80 in the polymer layer 200.

The PMMA block of the polymer layer 200 may be swollen by contacting the acetic acid, and the PMMA block 60 moves to an upper side of the PS block 40 and the nano pore 80 is formed in a center portion of the pillar-shaped PMMA block 60.

The single polymer is emitted to the acetic acid due to movement of the PMMA block 60.

Concentration of the acetic acid may be 10 wt % to 50 wt %. When the concentration of the acetic acid is less than 10 wt %, swollen of the PMMA block 60 may not occur.

After then nano pore 80 is formed, the substrate 5 may be eliminated and the polymer layer 200 may be fixed to the support member 100. However, the polymer layer 200 may be easily torn due to the nano pore 80, and therefore it is preferred to form the nano pore 80 after fixing the polymer layer 200 to the support member 100.

Meanwhile, a hole barrier layer (not shown) formed of gold (Au) and having a thickness of 2 nm may be further formed in the upper portion of the membrane. The hole barrier layer may be formed through thermal evaporation or E-beam sputtering.

The hole barrier layer is provided for accuracy in measurement of efficiency using the membrane having the nano pores as shown in FIG. 5 according to the exemplary embodiment of the present invention.

That is, when the membrane is formed through the method of FIG. 6 to FIG. 8, a PMMA block of which a terminal group is substituted by COOH is disposed in the upper side of the membrane. Thus, when the DNA is flown, the DNA is attached not only to the pores but to the upper side of the membrane and accordingly accuracy in measurement of efficiency shown in FIG. 5 may be deteriorated.

However, when the hole barrier layer is formed in the upper side of the membrane according to the exemplary embodiment of the present invention, the DNA is attached only into the pores so that accuracy in efficiency measurement can be improved.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

40: PSblock
60: PMMA block
80: nano pore
100: support member
200: polymer layer

What is claimed is:

1. A membrane manufacturing method comprising:

forming an alignment layer with poly(styrene-random-methyl methacrylate) (PS-ran-PMMA) on a substrate including a sacrificial layer;

forming a polymer layer by coating a solution including polystyrene-block-polymethyl methacrylate-di carboxylic acid (PS-b-PMMA-diCOOH) having a dicarboxyl group(-diCOOH) on the alignment layer; and forming a plurality of nano pores, each having an inner wall formed of a poly(methyl methacrylate) (PMMA) block of which the end thereof is substituted by at least one of carboxyl group (—COOH), amine group (—$NH_2$), and a thiol group (—SH) in the polymer layer by soaking the polymer layer in an acetic acid, wherein the solution including PS-b-PMMA-diCOOH further includes a PMMA single polymer, and wherein the solution including PS-b-PMMA-diCOOH is formed by mixing a polystyrene-block-poly(methyl methacrylate) block with a p-toluenesulfonic acid and hydrolyzing the mixture at 100° C. for 12 hours.

2. The membrane manufacturing method of claim 1, wherein the forming of the polymer layer further comprises coating the solution and performing heat treatment, and the heat treatment is performed at 170° C. for 24 hours.

3. The membrane manufacturing method of claim 1, wherein further comprising eliminating the sacrificial layer by etching after the forming of the nano pores.

4. The membrane manufacturing method of claim 3, wherein the sacrificial layer is formed of silicon oxide and eliminated by etching with a hydrofluoric acid solution.

5. The membrane manufacturing method of claim 4, wherein further comprising fixing the polymer layer on a support member after the eliminating of the sacrificial layer.

* * * * *